United States Patent [19]

Misato et al.

[11] 4,078,074
[45] Mar. 7, 1978

[54] 2H-CHROMENE-2-SPIRO-3'-PHTHALIDES USEFUL AS HORTICULTURAL AND AGRICULTURAL FUNGICIDES

[75] Inventors: Tomomasa Misato, Tokyo; Keido Ko, Wako; Yasuo Homma, Kawagoe; Kazuhiko Konno, Ami; Yosio Hayasi, Ami; Tetsuo Sekiya, Ami; Kozo Sato, Hatogaya, all of Japan

[73] Assignee: Rikagaku Kenkyusho and Mitsubishi Petrochemical Company Limited, Japan

[21] Appl. No.: 635,385

[22] Filed: Nov. 25, 1975

[30] Foreign Application Priority Data

Dec. 3, 1974  Japan ................. 49-138999

[51] Int. Cl.² ............... A01N 9/28; C07D 307/83; C07D 307/87
[52] U.S. Cl. ............... 424/279; 260/343.3 R
[58] Field of Search ............... 424/279; 260/343.3

[56] References Cited

U.S. PATENT DOCUMENTS

| 3,687,975 | 8/1972 | Houlihan | 260/343.3 |
| 3,766,214 | 10/1973 | Lin et al. | 260/343.3 |
| 3,767,673 | 10/1973 | Houlihan et al. | 260/343.3 |
| 3,812,181 | 5/1974 | Leimgruber et al. | 260/343.3 |
| 3,959,571 | 5/1976 | Yahagi et al. | 260/343.3 |

OTHER PUBLICATIONS

Chem. Abst. 49 5484 (e) (1955) Seher et al., Syntheses of Spiroheterocyclic compounds.

*Primary Examiner*—Albert T. Meyers
*Assistant Examiner*—D. W. Robinson
*Attorney, Agent, or Firm*—Bucknam and Archer

[57] ABSTRACT

The present invention provides a novel horticultural and agricultural fungicidal composition which contains as an effective component a 2H-chromene-2-spiro-3'-phthalide derivative and a method for killing fungus on plants.

23 Claims, No Drawings

2H-CHROMENE-2-SPIRO-3'-PHTHALIDES USEFUL AS HORTICULTURAL AND AGRICULTURAL FUNGICIDES

This invention relates to a novel agricultural and horticultural fungicide containing as an active ingredient a 2H-chromene-2-spiro-3'-phthalide derivative.

Organic phosphorus-containing chemicals and organic chlorine-containing chemicals have heretofore been used as agricultural and horticultural fungicides and bring about an increase in crop yield. However, their manufacture or use is now considerably limited and regulated because of soil contamination, phytotoxicity to plants, toxicity to men and domestic animals and residualability. Accordingly, development of novel fungicides has eagerly been desired in the art.

As a result of our prolonged and detailed research work, we found that 2H-chromene-2-spiro-3'-phthalide derivatives have a high fungicidal activity of fungi causing various plant diseases represented by blast on rice, powdery mildew and downy mildew on cucumber, gray mold and the like and that these derivatives have no phytotoxicity to plants and no toxicity to men and domestic animals. We have now completed this invention based on these findings.

A primary object of the present invention is to provide a novel horitcultural and agricultural fungicidal composition which contains as an effective component 2H-chromene-2-spiro-3'-phthalide derivative.

Another object of the present invention is to provide a method for killing fungus on plants by using the fungicidal composition mentioned above.

Still another object of the present invention is to provide a method for preventing plants from diseases caused by the fungus.

Other objects of the present invention are able to be understood easily by the skilled in the art on the basis of the description below.

More specifically, in accordance with this invention, there is provided an agricultural and horticultural fungicide containing as an active ingredient at least one compound represented by the following general formula (I):

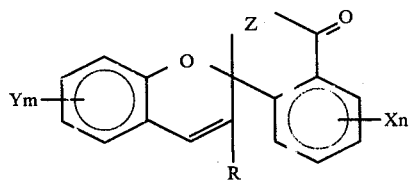
(I)

wherein
R stands for a hydrogen atom or a lower alkyl or aryl group,
Z stands for an oxygen atom or a substituted or unsubstituted imino group,
X and Y stand for a hydrogen or halogen atom, a lower hydrocarbon radical or an alkoxy, alkylthio, nitro or substituted or unsubstituted amino group where two Y's may be bonded together to form a group

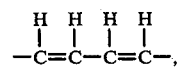

and
m and n stand for an integer of from 1 to 4 with the proviso that when m and n stand for an integer larger than 1, X's and Y's may be the same or different, X's may be the same as or different from each other and Y's may be the same as or different from each other.

In the above general formula (I), as the lower alkyl group as R, there can be mentioned alkyl groups having 1 to 4 carbon atoms, such as methyl, ethyl, propyl and butyl groups, and as the aryl group as R, there can be mentioned aryl groups having 6 to 9 carbon atoms, such as phenyl, toluyl and xylyl groups.

As the substituted imino group as Z, there can be mentioned imino groups having a substituent a lower alkyl group having 1 to 4 carbon atoms, an aryl group having 6 to 9 carbon atoms or a halogen-substituted aryl group, such as methylimino, ethylimino, propylimino, butylimino, phenylimino, toluylimino, and p-chlorophenyl imino groups.

As the halogen atom as X or Y, there can be mentioned chlorine, bromine and iodine, and as the lower hydrocarbon radical, there can be mentioned alkyl and alkenyl groups having 1 to 4 carbon atoms, such as methyl, ethyl, n-propyl, isopropyl, allyl and butyl groups wherein two Y's may be bonded together to form a group

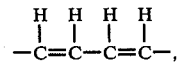

namely a naphthalene ring together with the benzene ring to which they are bonded (see compound (3) described below).

As the alkoxy group as X or Y, there can be mentioned saturated and unsaturated, linear and branched alkoxy groups having 1 to 4 carbon atoms, such as methoxy, ethoxy, propoxy and allyloxy groups. As the alkylthio group, there can be mentioned saturated and unsaturated alkylthio groups having 1 to 4 carbon atoms, such as methylthio, ethylthio, propylthio and allylthio groups.

As the most preferable compounds among the compounds having chemical formula (I) above mentioned, there are mentioned two groups of compound, one bearing oxygen atom as Z radical and the other bearing nitrogen atom as Z radical.

The former compounds are shown by the following chemical formula (II).

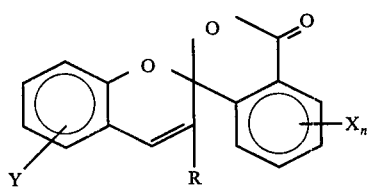
(II)

wherein
R stands for hydrogen atom, lower alkyl or aryl radical,
X stands for hydrogen or halogen atom,
Y stands for hydrogen or halogen atom, lower alkyl or alkoxy radical, alkyl substituted amine or nitro radical, or signifies radical —CH=CH—CH=•CH— which combines with the phenyl ring of 2H-chromene ring to form a benzo [f] -2H-chromene ring, and n signifies an integer of 1 to 4.

The latter compounds are shown by the chemical formula (III):

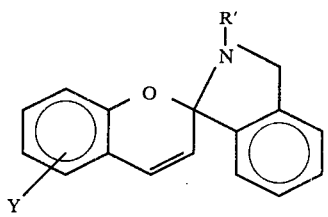

wherein R' stands for hydrogen atom or lower alkyl radical, and Y for hydrogen or halogen atoms.

Each radical in the compounds having the chemical formula (II) and (III) such as alkyl, alkoxy, aryl radical or halogen atom have the same meaning as in that of the chemical formula (I).

When the compounds are used as agricultural and horticultural fungicides, they may be applied directly or after they have been formed into suitable preparations, such as granules, dusts, wettable powders, tablets, oils and aerosols, by using suitable solid carriers, liquid crriers and emulsifiers according to known methods for prroduction of agricultural chemical preparations. As the carrier, there can be mentioned, for example, clay, kaolin, bentonite, acid clay, diatomaceous earth, calcium carbonate, nitrocellulose, starch, gum arabic, benzene, xylene, alcohols, acetone, keroxine, dimethylformamide and Freon. Further, adjuvants customarily used in this field, such as spreading agents, emulsifiers and surface active agents, e.g., soaps, sulfuric acid esters of higher alcohol, alkylsulfonates, alkylarylsulfonates, quaternary ammonium salts and polyalkylene oxides, may optionally be incorporated in the fungicides of the present invention. The content of the active ingredient of above general formula (I) is preferably about 10 to about 90% in the case of emulsifiable liquids and wettable powders, and it is preferably about 0.1 to about 10% in the case of dusts and oils. Of course, the concentration of the active compound may optionally be changed depending on the disease to be controlled. The fungicide of the present invention may be applied in admixture with other agricultural chemicals, a fertilizer such as urea, ammonium sulfate, a potassium salt or the like and a soil modifier as necessary.

The present fungicial composition has a preventing effect on the diseases of plant and fruits thereof caused by fungus and a killing effect on fungus on plants and fruits thereof. As example of plants on which the present fungicidal composition is effective there can be mentioned such fruit-bearing plants as grape and melon vines, tangerine, orange and apple trees and food crops such as rice plant and vegetables in common, for example cucumbers, egg-plants, tomatoes, cayene-pepper and Spanish paprika, etc. The present fungicidal composition is effective not only against fungus growth on the leaves, branches, and stems of plants, but also against growths on their fruits.

More particularly, the diseases of plants prevented and cured by the present fungicidal composition are illustrated as below:

Phthophtora rot of cucumber, egg-plant and melon vines; Late blight of tomato; Phythophthora blight of cayenne-pepper and Spanish paprika; Anthracnose of cucumber, egg-plant, and tomato; Downy mildew of cucumber, egg-plant and Spanish paprika; Powery mildew of cucumber, egg-plant, and Spanish paprike; Gray mold of vegetables in common; Anthracnose of grapevine; and Gray mold of apple tree and citrus and so on.

To kill the fungus on plants and prevent plants from the diseases caused by the fungus, the present fungicidal composition is sprayed in an amount of about 2 kg to 5 per 10 are in the case of dust, and is sprayed in an amount of 100 to 500 ppm of active component in the case of wettable powder and emulsion.

Typical compounds represented by the general formula (I), are shown in Table 1. Compound numbers given in this Table 1 are used uniformly throughout the instant specification.

Table 1

| Compound No. | Name |
|---|---|
| (1) | 2H-chromene-2-spiro-3'-phthalide |
| (2) | 6-bromo-2H-chromene-2-spiro-3'-phthalide |
| (3) | Benzo[f]-2H-chromene-2-spiro-3'-phthalide |
| (4) | 6-nitro-2H-chromene-2-spiro-3'-phthalide |
| (5) | 8-methoxy-2H-chromene-2-spiro-3'-phthalide |
| (6) | 6-chloro-2H-chromene-2-spiro-3'-phthalide |
| (7) | 6-methyl-2H-chromene-2-spiro-3'-phthalide |

Table 1-continued

| Compound No. | Name |
|---|---|
| (8) | 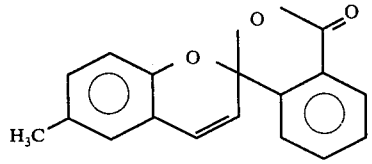 6-methoxy-2H-chromene-2-spiro-3'-phthalide |
| (9) | 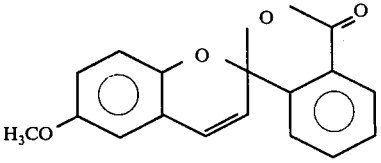 6-nitro-2H-chromene-2-spiro-3'-(4',5',6',7'-tetrachlorophthalide) |
| (10) | 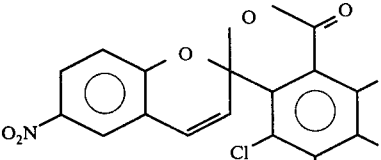 7-N,N-dimethylamino-2H-chromene-2-spiro-3'-(4',5',6',7'-tetrachlorophthalide) |
| (11) | 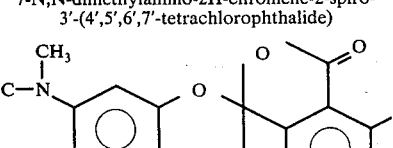 3-methyl-2H-chromene-2-spiro-3'-phthalide |
| (12) | 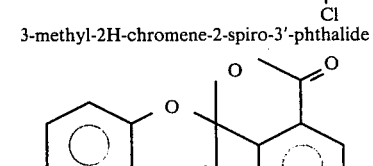 7-N,N-dimethylamino-3-methyl-2H-chromene-2-spiro-3'-phthalide |
| (13) | 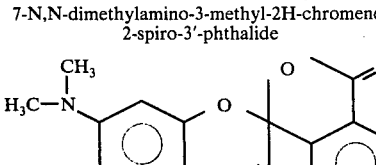 6-nitro-3-methyl-2H-chromene-2-spiro-3'-phthalide |
| (14) | 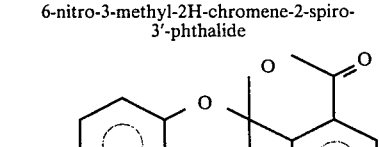 3-phenyl-2H-chromene-2-spiro-3'-phthalide |
| (15) | 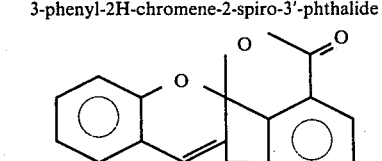 7-N,N-dimethylamino-3-methyl-2H-chromene-2-spiro-3'-phthalimidine |

Table 1-continued

| Compound No. | Name |
|---|---|
| (16) | 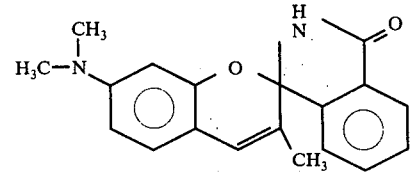 2H-chromene-2-spiro-3'-(2'-methylphthalimidine) |
| (17) | 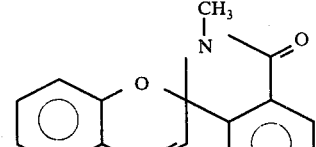 6-bromo-2H-chromene-2-spiro-3'-(2'-methylphthalimidine) |
| (18) | 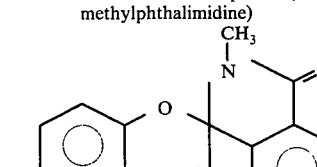 6-nitro-2H-chromene-2-spiro-3'-(2'-methylphthalimidine) |
| (19) | 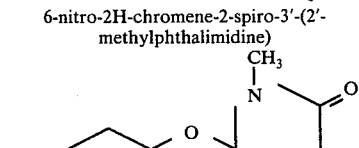 6-methylthio-2H-chromene-2-spiro-3'-phthalide |
| (20) | 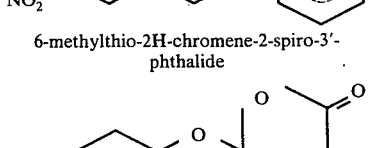 8-amino-2H-chromene-2-spiro-3'-phthalide |
| (21) | 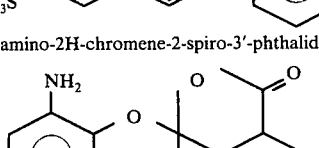 2H-chromene-2-spiro-3'-(7'-nitrophthalide) |
| (22) | 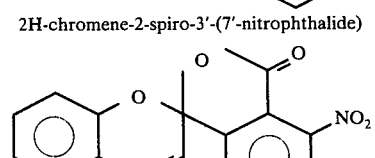 6-methoxy-2H-chromene-2-spiro-3'-(7'-ethylphthalide) |
| (23) | 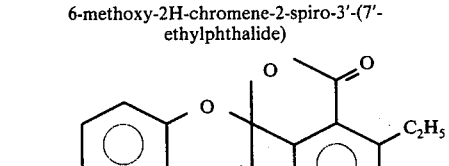 3-n-propyl-2H-chromene-2-spiro-3'-(7'-N,N-dimethylaminophthalide) |

Table 1-continued

| Compound No. | Name |
|---|---|
| (24) | 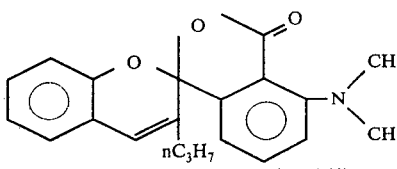 7-amino-2H-chromene-2-spiro-3'-(6'-methoxyphthalide) |
| (25) | 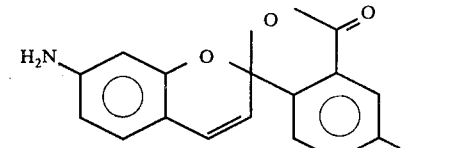 2H-chromene-2-spiro-3'-phthalimidine |
| (26) | 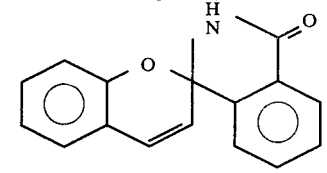 6-fluoro-2H-chromene-2-spiro-3'-(6'-methoxyphthalimidine) |
| (27) | 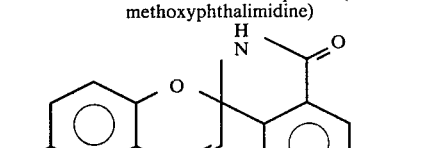 8-methylthio-2H-chromene-2-spiro-3'-(2'-ethyl-7'-nitrophthalimidine) |
| (28) | 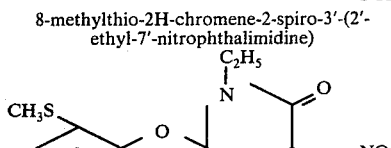 6-methyl-2H-chromene-2-spiro-3'-(2'-butyl-7'-N,N-dimethylaminophthalimidine) |
| (29) | 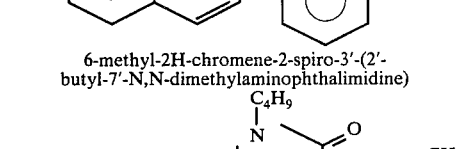 6-vinyl-8-methylthio-2H-chromene-2-spiro-3'-phthalide |
| (30) | 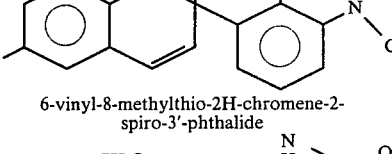 2H-chromene-2-spiro-3'-(2'-phenyl-phthalimidine) |

Table 1-continued

| Compound No. | Name |
|---|---|
| (31) | 6-methyl-8-bromo-2H-chromene-2-spiro-3'-(2'-phenylphthalimidine) 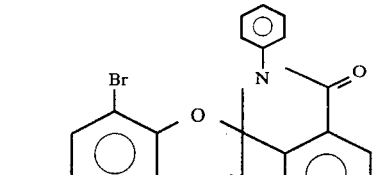 |
| (32) | 2H-chromene-2-spiro-3'-(2'-p-chlorophenylphthalimidine) 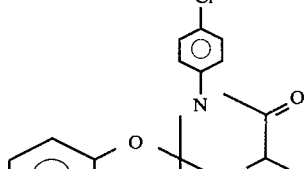 |

The foregoing compounds (1) – (14) can be synthesized in good yields with ease by heating corresonding o-(o-hydroxycinnamoyl)benzoic acid derivatives in a polar solvent and the compounds (15) – (32) by reacting corresponding salicylaldehydes with o-acylbenzoic acid derivatives (for example, amides) under acidic conditions.

Synthesis of the foregoing compounds will now be described with reference to the following Synthesis Examples.

SYNTHESIS EXAMPLE 1

12.7 g of o-(o-hydroxycinnamoyl)benzoic acid was heated in 100 ml of N-dimethylformamide under agitation for 6 hours. Then, the liquid reaction mixture was poured into 400 ml of water to form a white crystal. The crystal was recovered by filtration and recrystallized from ethyl alcohol to obtain 10.7 g of 2H-chromene-2-spiro-3'-phthalide (compound (1)) as a colorless needle. (yield = 90%). Physical properties of the product are as follows:

Melting Point: 113° – 114° C.
Elementary Analysis Values as $C_{16}H_{10}O_3$:

| | C(%) | H(%) |
|---|---|---|
| Found: | 76.70 | 4.15 |
| Calculated: | 76.79 | 4.03 |

SYNTHESIS EXAMPLE 2

In 50 ml of concentrated sulfuric acid, 6.1g of o-salicylaldehyde was reacted with 8.9 g of N-methyl-o-acetylbenzoic acid at room temperature for 4 hours under agitation. Then, the liquid reaction mixture was gradually poured into 400 ml of ice water, and the precipitated crystal was recovered by filtration, washed sufficiently with water and recrystallized from ethyl alcohol to obtain 9.2 g (yield = 70%) of 2H-chromene-2-spiro-3'-(2'-methylphthalimidine) (compound (16)) as a white crystal. Physical properties of the product are as follows:

Melting Point: 121.5° C.
Elementary Analysis Values as $C_{17}H_{13}NO_2$:

|  | C(%) | H(%) | N(%) |
|---|---|---|---|
| Found : | 77.49 | 5.04 | 5.31 |
| Calculated: | 77.55 | 4.98 | 5.32 |

The present invention will now be described in reference to the following Examples. We do not intend to limit the scope of the invention by these examples. In these Examples, all of "parts" are shown by weight.

EXAMPLE 1 (Wettable Powder)

| Compound (1) | 50 parts |
|---|---|
| Sodium alkylsulfate | 5 parts |
| Diatomaceous earth | 45 parts | were uniformly blended to obtain a wettable powder having an active ingredient concentration of 50%. On application, the wettable powder was diluted with water to a prescribed concentration and then scattered.

EXAMPLE 2 (Emulsifiable Liquid)

| Compound (1) | 20 parts |
|---|---|
| Xylene | 40 parts |
| Cyclohexanone | 35 parts |
| Polyoxyethylene phenyl ether | 5 parts | were sufficiently mixed to obtain an emulsifiable liquid having an active ingredient concentration of 20%. On application, it was diluted with water to a prescribed concentration and then scattered.

EXAMPLE 3 (Dust)

| Compound (1) | 2 parts |
|---|---|
| Talc | 98 parts | were uniformly mixed and the mixture was pulverized to obtain a dust having an active ingredient concentration of 2%. On application, the so formed dust was directly scattered.

The effects of the fungicide of the present invention will now be shown in reference to the following Tests.

TEST EXAMPLE 1 (Test on Effect for Controlling Blast on Rice Plant)

Unhulled grains of paddy rice (variety: Jukkoku) were sown in cultivation pots (10 grains per pot) and a wettable powder prepared according to the method described in Example 1 was applied to said rice plants at the 4- of 5-leaved stage and after drying, a suspension of spores of a blast-causing fungus (*Pyrcularia oryzae*) was sprayed on the chemical-applied rice plants. The spore suspension used for inoculation was one obtained by culturing the pathogenic fungus in a rice hull medium (comprising 3 g of rice hull, 0.01 g of powdery yeast extract, 0.2 g of sugar, 0.05 g of starch and 5 ml of water) at 27° C. for 7 to 10 days. The inoculation was conducted in an inoculation box by spraying. After the inoculation, the rice plants were allowed to stand still in an air-conditioned box for 24 hours at 25° C., and then, they were allowed to stand still on a vat filled with water and were covered by a vinyl resin tent. After 5 to 7 days from the inoculation, the rice plants showed the symptoms of the diseases. At this stage, the number of stigmata or disease specks per pot was counted and the control value was calculated according to the following equation:

$$\text{Control value} = \left(\frac{A - B}{A}\right) \times 100 \, (\%)$$

wherein A denotes the number of stigmata in the untreated area and B denotes the number of stigmata in the chemical applied area.

Results are shown in Table 2.

Incidentally, the number of stigmata in the untreated area was 230 in this test.

Table 2

| Chemical Applied (Compound No.) | Melting Point (° C.) | Applied Concentration (ppm) | Control Value (%) | Phytotoxicity |
|---|---|---|---|---|
| 1 | 113–114 | 1,000 | 98 | not observed |
| 2 | 196–196.5 | 1,000 | 85 | not observed |
| 3 | 214–215 | 1,000 | 80 | not observed |
| 4 | 208.5–210.5 | 1,000 | 68 | not observed |
| 5 | 209–210.5 | 1,000 | 82 | not observed |
| 6 | 187–187.5 | 1,000 | 72 | not observed |
| 7 | 195.5 | 1,000 | 75 | not observed |
| 8 | 202–203 | 1,000 | 70 | not observed |
| 9 | 236.5–237 | 1,000 | 84 | not observed |
| 10 | 235 (decomposition) | 1,000 | 85 | not observed |
| 11 | 78–79 | 1,000 | 82 | not observed |
| 12 | 189.5 | 1,000 | 87 | not observed |
| 13 | 200 | 1,000 | 75 | not observed |
| 14 | 147–148.5 | 1,000 | 89 | not observed |
| 15 | 205.5–206 | 1,000 | 85 | not observed |
| 16 | 121.5 | 1,000 | 96 | not observed |
| 17 | 138–138.5 | 1,000 | 72 | not observed |
| 18 | 200–201 | 1,000 | 74 | not observed |

TEST EXAMPLE 2 (Test on Effect for Controlling Powdery Mildew on Cucumber)

When about 20 days had passed from sowing of seeds of cucumber (variety: Sagami Hansiro), a wettable powder prepared according to the method described in Example 1 was applied to seedlings. After the applied chemical had dried, a powdery mildew-causing fungus (*Sphaerotheca fuliginea* Pollacci) was inoculated on the seedlings in the following manner:

Conidia were let to fall in a Petri dish from surfaces of leaves cucumber suffering from powdery mildew by a writing brush, and they were suspended in distilled water so that the number of conidia in one visible area (under a microscope of 100 magnifications) was about 100. The resulting spore suspension was inoculated on the seedlings in an inoculation box by spraying.

Then, the inoculated seedlings were allowed to stand still in a temperature-adjusted vinyl film green house. When about 12 days had passed from the inoculation, the number of deseased spots was examined and the control value was calculated. In each of the chemical treating area, 10 seedlings were used. The calculation of the control value was conducted in the same manner as described in Test 1. Incidentally, the number of deseased spots stigmata in the untreated area was 480 in this test.

Results are shown in Table 3.

Table 3

| Applied Chemical (Compound No.) | Applied Concentration (ppm) | Control Value (%) | Phytotoxicity |
| --- | --- | --- | --- |
| 1 | 1,000 | 98 | not observed |
| 2 | 1,000 | 88 | not observed |
| 3 | 1,000 | 79 | not observed |
| 4 | 1,000 | 65 | not observed |
| 5 | 1,000 | 88 | not observed |
| 6 | 1,000 | 78 | not observed |
| 7 | 1,000 | 77 | not observed |
| 8 | 1,000 | 75 | not observed |
| 9 | 1,000 | 82 | not observed |
| 10 | 1,000 | 92 | not observed |
| 11 | 1,000 | 90 | not observed |
| 12 | 1,000 | 87 | not observed |
| 13 | 1,000 | 80 | not observed |
| 14 | 1,000 | 85 | not observed |
| 15 | 1,000 | 86 | not observed |
| 16 | 1,000 | 92 | not observed |
| 17 | 1,000 | 75 | not observed |
| 18 | 1,000 | 78 | not observed |

TEST EXAMPLE 3 (Test on Effects for Controlling Several Deseases of Cucumber)

Cucumber seedlings (Sagamihansiro) grown for three weeks after sowing seeds were set in vinyl house. Fourteen seedling were set in one test section and three test sections were settled. These seedlings of cucumber were grown under a condition under which Downy mildew or Powdery mildew were naturally developed. Water dispersion of wettable powder of Compound 1 prepared according to Example 1 were sprayed five times on the seedlings in an amount of 100 liter/10a are after one week had been passed from setting. After one week from the last spraying of water dispersion, number of opened leaves deseased were counted on each test seedling in each test section, and calculated desease ratio and control ratio are calculated. The results obtained are shown in Table 4. Each value is a mean value of the values obtained in each test section.

Table 4

| Compound Tested | Spayed Amounts (ppm) | disease value | | Control value | |
| --- | --- | --- | --- | --- | --- |
| | | Powdery Mildew | Downy Mildew | Powdery Mildew | Downey Mildew |
| 1 | 400 | 0 | 0 | 100 | 100 |
| 1 | 200 | 0 | 0 | 100 | 100 |
| non-treated | | 80 | 40 | — | — |

What we claim are:

1. An agricultural and horticultural fungicidal composition in the form of a wettable powder, an emulsifiable liquid or a dust containing at least one compound of the formula

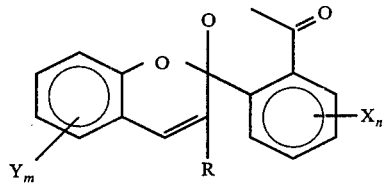

(II)

wherein
R stands for hydrogen, lower alkyl or aryl;
X stands for hydrogen, lower alkyl or halogen;
Y stands for a hydrogen, halogen, lower alkyl, alkyl substituted amino, nitro, alkoxy group, or $$-\overset{H}{\underset{|}{C}}=\overset{H}{\underset{|}{C}}-\overset{H}{\underset{|}{C}}=\overset{H}{\underset{|}{C}}-$$

which together with the phenyl ring in said 2H-chromeme ring forms a benzo [f]—2H-chromene ring, m and n stand for an integer of 1 to 4, in the amount of 0.1–90% and inert components selected from the group of (a) an organic solvent and a surface active agent (b) a solid carrier and (c) a surface active agent and a solid carrier.

2. The agricultural and horticultural fungicidal composition of claim 1, containing as an effective component 2H-chromene-2-spiro-3'-phthalide.

3. The agricultural and horticultural fungicidal composition of claim 1, containing as the effective component 6-bromo-2H-chromene-2-spiro-3'-phthalide.

4. The agricultural and horticultural fungicidal composition of claim 1, containing as the effective component Benzo[f]-2H-chromene-2-spiro-3'-phthalide.

5. The agricultural and horticultural fungicidal composition of claim 1, containing as the effective component 6-nitro-2H-chromene-2-spiro-3'-phthalide.

6. The agricultural and horticultural fungicidal composition of claim 1, containing as the effective component 8-methoxy-2H-chromene-2-spiro-3'-phthalide.

7. The agricultural and horticultural fungicidal composition of claim 1, containing as the effective component 6-chloro-2H-chromene-2-spiro-3'-phthalide.

8. The agricultural and horticultural fungicidal composition of claim 1, containing as the effective component 6-methyl-2H-chromene-2-spiro-3'-phthalide.

9. The agricultural and horticultural fungicidal composition of claim 1, containing as the effective component 6-methoxy-2H-chromene-2-spiro-3'-phthalide.

10. The agricultural and horticultural fungicidal composition of claim 1, containing as the effective component 6-nitro-2H-chromene-2-spiro-3'-(4',5',6',7'-tetrachlorophthalide).

11. The agricultural and horticultural fungicidal composition of claim 1, containing as the effective component 7-N,N-dimethylamino-2H-chromene-2-spiro-3'-(4',5',6',7'-tetrachlorophthalide).

12. The agricultural and horticultural fungicidal composition of claim 1, containing as the effective component 3-methyl-2H-chromene-2-spiro-3'-phthalide.

13. The agricultural and horticultural fungicidal composition of claim 1, containing as the effective component 7-N,N-dimethylamino-3-methyl-2H-chromene-2-spiro-3'-phthalide.

14. The agricultural and horticultural fungicidal composition of claim 1, containing as the effective component 6-nitro-3-methyl-2H-chromene-2-spiro-3'-phthalide.

15. The agricultural and horticultural fungicidal composition of claim 1, containing as the effective component 2-phenyl-2H-chromene-2-spiro-3'-phthalide.

16. An agricultural and horticultural fungicidal composition according to claim 1 which is in the form of an emulsifiable liquid containing said effective component in the amount of about 10 to 90 percent in weight, an organic solvent and a surface active agent in an amount effective to produce an emulsifiable liquid.

17. An agricultural and horticultural fungicidal composition according to claim 1 which is in the form of wettable powder comprising said effective component in the amount of about 10 to 90 percent in weight, a surface active agent and a solid carrier.

18. An agricultural and horticultural fungicidal composition according to claim 1 which is in the form of dust comprising said effective component in an amount of about 0.1 to 10 percent in weight and a solid carrier.

19. A method of protecting plants from attack by fungi which comprises applying to said plants susceptible to said fungi attack a fungicidally effective amount of at least one compound of the formula

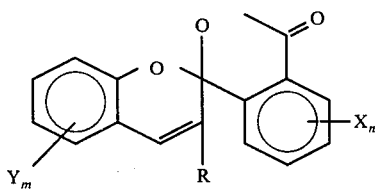
(II)

wherein
R stands for hydrogen, lower alkyl or aryl,
X stands for hydrogen, halogen or lower alkyl,
Y stands for hydrogen, halogen, lower alkyl, alkyl substituted amino, nitro, alkoxy group, or

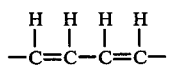

which together with the phenyl ring in said 2H-chromeme ring forms a benzo [f]-2H-chromene ring, m and n stand for an integer of 1 to 4.

20. A method of protecting plants according to claim 19 wherein said at least one compound is applied in the form of an horticultural and agricultural composition which is applied in the form of a dust in the amount of 2-5 kg. per 10 are.

21. A method of protecting plants according to claim 19 wherein said at least one compound is applied as an horticultural and agricultural composition which is applied in the form of a wettable powder or emulsion wherein said compound is present in an amount of 100-500 ppm.

22. A method of killing fungi on plants affected by said fungi which comprises applying to said fungi a fungicidally effective amount of a compound of the formula

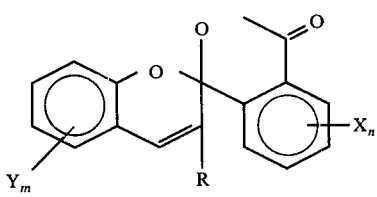
(II)

wherein
R stands for hydrogen, lower alkyl or aryl,
X stands for hydrogen, lower alkyl or halogen,
Y stands for a hydrogen, halogen, lower alkyl, alkyl substituted amino, nitro, alkoxy group, or

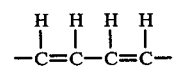

which together with the phenyl ring in said 2H-chromeme ring forms a benzo[f]—2-chromene ring, m and n stands for an integer of 1 to 4.

23. A method of killing fungi on plants according to claim 22 wherein said effective compound is applied in the form of an agricultural and horticultural composition which is applied as a dust in an amount of 2-5 kg. per 10 are.

* * * * *